US005686616A

United States Patent [19]
Tani et al.

[11] Patent Number: 5,686,616
[45] Date of Patent: Nov. 11, 1997

[54] PROCESS FOR PREPARING AN OPTICALLY ACTIVE AMINE

[75] Inventors: Kazuhide Tani, Hyogo; Tsuneaki Yamagata; Yasutaka Kataoka, both of Osaka; Hidenori Kumobayashi, Kanagawa, all of Japan

[73] Assignee: Takasago International Corporation, Tokyo, Japan

[21] Appl. No.: 615,410

[22] Filed: Mar. 14, 1996

[30] Foreign Application Priority Data

Mar. 14, 1995 [JP] Japan ................................. 7-080829
Jan. 31, 1996 [JP] Japan ................................. 8-035728

[51] Int. Cl.$^6$ ................ C07C 209/52; C07D 211/02
[52] U.S. Cl. ................ 546/185; 546/150; 546/166; 548/482; 548/490; 564/385; 564/387; 564/392; 564/398; 564/415; 564/448; 564/489
[58] Field of Search .................... 564/385, 387, 564/392, 398, 415, 448, 489; 546/150, 166, 185; 548/482, 490

[56] References Cited

U.S. PATENT DOCUMENTS

| | | | |
|---|---|---|---|
| 4,556,740 | 12/1985 | Hansen et al. ............................. | 568/13 |
| 4,965,348 | 10/1990 | Saulnier et al. ........................ | 536/17.2 |
| 5,047,704 | 9/1991 | Yamachi et al. ........................ | 318/801 |
| 5,159,093 | 10/1992 | Taketomi et al. ....................... | 556/136 |
| 5,206,399 | 4/1993 | Sayo et al. ............................... | 556/20 |
| 5,223,632 | 6/1993 | Ishizaki et al. ........................... | 556/12 |
| 5,302,738 | 4/1994 | Foricher et al. ........................ | 558/162 |

FOREIGN PATENT DOCUMENTS

| | | |
|---|---|---|
| 35494 | 1/1991 | Japan . |
| 415796 | 3/1992 | Japan . |

OTHER PUBLICATIONS

Chemical Reviews, pp. 1663–1679 (1989).
Asymmetric Catalysis in Organic Synthesis, John Wiley & Sons, Inc. (1994).
James D. Morrison, Asymmetric Synthesis, vol. 5, Academic Press Inc. (1985).
Wagner and Zook, Synthetic Organic Chemistry, Chapter 25—Imines, John Wiley & Sons, Inc., New York; (1953).
Greene and Wuts, Protective Groups in Organic Synthesis, Second Edition, John Wiley & Sons, Inc., New York, pp. 272–275 and 364–369 (1991).
K.N. Campbell, A.H. Sommers and B.K. Campbell, J. Am. Chem. Soc., 66, 82 (1944).
G. Reddelien, Ber. 43, 2476 (1910).
J.H. Billman and K.M. Tai, J. Org. Chem., 23, 535 (1958).
S.R. Sandler and W. Karo, Organic Functional GroupPreparations, vol. 2, 246, Academic (1971).
S. Dayagi in The Chemistry of the Carbon–Nitrogen Double Bond, ed. By S. Patai, Wiley–Interscience, p. 61 (1970).
H. Takaya et al., J. Org. Chem., vol. 51, 629 (1986).
Chem. Pharm. Bull., p. 1085, vol. 39 (1991).
Synlett, p. 827 (1991).
Tetrahedron: Asymmetry, vol. 3 (1992).
J.L. Herde, J.C. Lambert and C.V. Senoff in Inorg. Synth., 15 (1974).
A. L. Onderdelinden, Inorg. Chim. Acta, 6, 420 (1972).
S.S. Bath and L. Vaska, J. Chem. Soc., 85, 3500 (1963).
M. Green et al., J. Chem. Soc., (A) 2334 (1971).
M.A. Bennett and D.L. Milner, J. Am. Chem. Soc., 91, 6983 (1969).

*Primary Examiner*—Richard L. Raymond
*Attorney, Agent, or Firm*—Sughrue,Mion,Zinn,Macpeak & Seas, PLLC

[57] ABSTRACT

A novel process for preparing an optically active amine by asymmetric hydrogenation of an imine compound, such as an imine compound prepared by condensing benzylamine and acetophenone, in the presence of a catalytic amount of an iridium-optically active phosphine complex and benzylamine or a benzylamine derivative. The present invention provides an optically active amine of high optical purity.

17 Claims, No Drawings

PROCESS FOR PREPARING AN OPTICALLY ACTIVE AMINE

BACKGROUND OF THE INVENTION

1. Field of the Invention

The present invention relates to a process for preparing an optically active amine which is useful as an optically active intermediate for medical drug synthesis or as an optical resolution agent for racemic modification of a carboxylic acid.

2. Description of the Related Art

Conventionally, an optically active amine compound has been obtained, for example, by optical resolution of a naturally derived amine compound or by optical resolution of a synthesized racemic modification of an amine compound using an optically active carboxylic acid. Recently, asymmetric catalytic synthesis techniques have been widely investigated as reported in the following: Sheri L. Blystone, *Chemical Reviews*, pp. 1663–1679 (1989); R. Noyori, *Asymmetric Catalysis in Organic Synthesis*, John Wiley & Sons, Inc. (1994); and James D. Morrison, *Asymmetric Synthesis*, Vol. 5, Academic Press Inc. (1985).

SUMMARY OF THE INVENTION

As mentioned above, some processes have been developed for preparing an optically active amine by asymmetric synthesis using a transition metal complex as a catalyst. However, in certain cases both the catalytic activity and enantiomeric excess are low depending on the particular substrate that is subjected to these processes. Therefore, an object of the present invention is to provide a novel process for preparing an optically active amine which solves the above described problems and which satisfies the needs of the industrial community.

DESCRIPTION OF THE PREFERRED EMBODIMENTS

As the result of extensive studies in view of the problems of the prior art, the present inventors have achieved the above objectives by providing a novel process for preparing an optically active amine which comprises asymmetrically hydrogenating an imine having the following general formula (I) in the presence of a catalytic amount of an iridium-optically active phosphine complex and benzylamine or a benzylamine derivative:

(I)

wherein $R^1$, $R^2$ and $R^3$ each represents (i) an aromatic hydrocarbon group which may be substituted with a halogen atom (e.g., Cl, Br, I), a lower alkyl group or a lower alkoxy group, (ii) an aliphatic hydrocarbon group which may be substituted with a halogen atom (e.g., Cl, Br, I), a lower alkyl group, a lower alkoxy group or said aromatic hydrocarbon group, or (iii) an alicyclic hydrocarbon group which may be substituted with a halogen atom (e.g., Cl, Br, I), a lower alkyl group, a lower alkoxy group or said aromatic hydrocarbon group, and two of $R^1$, $R^2$ and $R^3$ may bond together to form a 5- or 6-membered ring. The process of the present invention provides an optically active amine compound of high optical purity.

The following is a description of the imine compounds for use as a substrate in the present invention having the general formula (I):

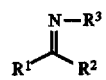
(I)

wherein $R^1$, $R^2$ and $R^3$ are as defined above.

The aromatic hydrocarbon group represented by $R^1$, $R^2$ and $R^3$ is preferably a $C_{6-10}$ aromatic hydrocarbon group (e.g., phenyl, naphthyl). Examples of the aromatic hydrocarbon group substituted with a halogen atom include 2-chlorophenyl, 3-chlorophenyl, 2,4-dichlorophenyl, 4-chlorophenyl, 3-bromophenyl, 4-bromophenyl, 4-iodophenyl, 6-chloronaphthyl, 7-chloronaphthyl, 6-bromonaphthyl, and 7-bromonaphthyl. The lower alkyl substituent of the aromatic hydrocarbon group is preferably a $C_{1-4}$ alkyl group. The lower alkoxy substituent of the aromatic hydrocarbon group represented by $R^1$, $R^2$ and $R^3$ is preferably a $C_{1-4}$ alkoxy group.

The aliphatic hydrocarbon group represented by $R^1$, $R^2$ and $R^3$ is preferably a $C_{1-4}$ aliphatic hydrocarbon group. Examples thereof include methyl, ethyl, propyl, butyl, isopropyl, t-butyl and sec-butyl. Examples of the aliphatic hydrocarbon group substituted with a halogen atom include chloromethyl and chloropropyl. The lower alkyl substituent of the aliphatic hydrocarbon group is preferably a $C_{1-20}$ alkyl group. Examples of the aliphatic hydrocarbon group substituted with a lower alkyl group include triphenylmethyl. The lower alkoxy substituent of the aliphatic hydrocarbon group is preferably a $C_{1-7}$ alkoxy group. Examples of the aliphatic hydrocarbon group substituted with a lower alkoxy group include benzyloxy.

The alicyclic hydrocarbon group represented by $R^1$, $R^2$ and $R^3$ is preferably a $C_{3-7}$ alicyclic hydrocarbon group. Examples thereof include cyclopropyl, cyclobutyl, cyclopentyl, cyclohexyl and cycloheptyl. Examples of the alicyclic hydrocarbon group substituted with a halogen atom include 2-chlorocyclohexyl, 3-chlorocyclohexyl, 4-chlorocyclohexyl, 2-chlorocyclopentyl and 3-chlorocyclopentyl. The lower alkyl substituent of the alicyclic hydrocarbon group is preferably a $C_{1-4}$ alkyl group. The lower alkoxy substituent of the alicyclic hydrocarbon group is preferably a $C_{1-7}$ alkoxy group.

Examples of the 5- or 6-membered ring formed when two of $R^1$, $R^2$ and $R^3$ bond together include

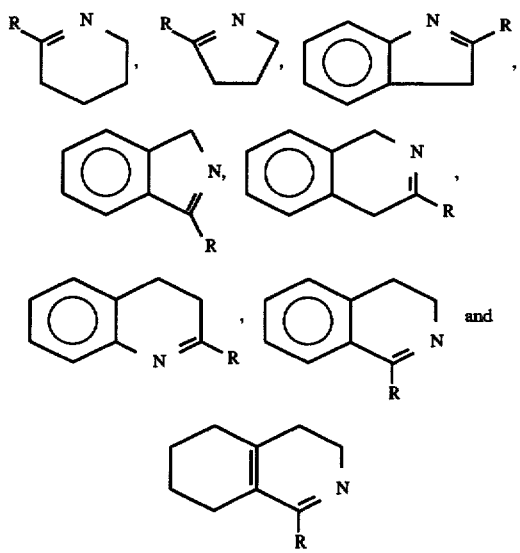

where R is lower alkyl, phenyl or benzyl which may be further substituted with a halogen atom, an alkyl group or an alkoxy group.

Examples of imine compounds for use in the present invention include those which are synthesized from lo benzylamine and which have been condensed with acetophenone, propiophenone, phenylpropylketone, phenylacetone, chloroacetone, α-methoxyacetone, α-hydroxyacetone, methylbutylketone, isopropylmethylketone, 1-indanone, 2-indanone, 1-tetralone, 2-tetralone, and the like. See, for example, Wagner and Zook, *Synthetic Organic Chemistry*, Chapter 25—Imines, John Wiley & Sons, Inc., New York.

Other examples of cyclic imine compounds for use in the present invention are 3,4-dihydro-5-methyl-2H-pyrrole, 5-n-butyl-3,4-dihydro-2H-pyrrole, 3,4-dihydro-5-ethyl-2H-pyrrole, 3,4-dihydro-5-phenyl-2H-pyrrole, 2-methyl-3,4,5,6-tetrahydropyridine, 2-phenyl-3,4,5,6-tetrahydropyridine, and the like.

For synthesizing an imine from an amine and a ketone so as to allow for asymmetric hydrogenation, the amine compound is such that it can easily release a group. Examples of the amine compound include, for example, benzylamine, 3,4-dimethoxy benzylamine, o-nitrobenzylamine, di(p-methoxyphenyl)methylamine, triphenylmethylamine, p-methoxyphenyldiphenylmethylamine, 5-dibenzosuberylamine, and the like. The preparation of n-benzyl and imine derivatives is described in Greene and Wuts, *Protective Groups in Organic Synthesis*, Second Edition, John Wiley & Sons, Inc., New York, pp. 272–275 and 364–369 (1991).

Details for preparation of the imine compound are also given in K. N. Campbell, A. H. Sommers and B. K. Campbell, *J. Am. Chem. Soc.*, 66, 82 (1944), G. Reddelien, *Ber.* 43, 2476 (1910), J. H. Billman and K. M. Tai, *J. Org. Chem.*, 23, 535 (1958), S. R. Sandler and W. Karo, *Organic Functional Group Preparations*, vol. 2, 246, Academic (1971), and S. Dayagi and V. Dagani in *The Chemistry of the Carbon-Nitrogen Double Bond*, ed. by S. Patai, Wiley-Interscience, p. 61, (1970).

The optically active phosphine compounds for use as a catalyst when complexed with iridium include those materials which are known in the art, and compounds of general formula (II) are particularly preferred:

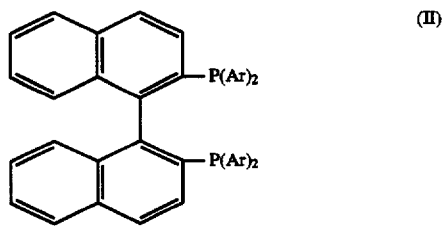
(II)

wherein Ar is a phenyl group which may be para- and/or meta-substituted with one or more lower alkyl (e.g., $C_{1-4}$) groups. Specific examples of the optically active phosphine compound include 2,2'-bis(diphenylphosphino)-1,1'-binaphthyl, 2,2'-bis(di-p-tolylphosphino)-1,1'-binaphthyl, 2,2'-bis(di-m-tolylphosphino)-1,1'-binaphthyl, 2,2'-bis(3,5-dimethylphenylphosphino)-1,1'-binaphthyl, 2,2'-bis(di-p-tert-butylphosphino)-1,1'-binaphthyl, and the like.

Further in this regard, the synthesis of 3,5-dimethyl BINAP is described in U.S. Pat. No. 5,223,632, and the synthesis of p-tert-Butyl BINAP is described in H. Takaya et al., *J. Org. Chem.*, vol. 51, 629 (1986).

In addition, examples of the phosphine compound for use in the present invention include those represented by general formula (III):

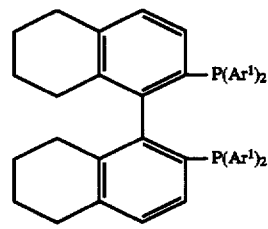
(III)

wherein $Ar^1$ is a p-methoxyphenyl, phenyl, p-tolyl, m-tolyl, p-chlorophenyl or 3,5-xylyl group.

Specific examples of the phosphine compound represented by formula (III) include 2,2'-bis(diphenylphosphino)-1,1' bi(5,5',6,6',7,7',8,8'-octahydronaphthyl), 2,2'-bis(di-p-tolylphosphino)1,1'-bi(5,5',6,6',7,7',8,8'-octahydrobinaphthyl),2,2'-bis(di-m-tolylphosphino)-1,1'-bi(5,5',6,6',7,7',8,8'-octahydronaphthyl), 2,2'-bis(di-p-chlorophenylphosphino)-1,1'-bi(5,5',6,6',7,7',8,8'-octahydronaphthyl), 2,2'-bis(di-3,5-xylylphosphino)-1,1'-bi(5,5',6,6',7,7',8,8'-octahydronaphthyl), 2,2'-bis(di-p-methoxyphenylphosphino)-1,1'-bi(5,5',6,6',7,7',8,8'-octahydronaphthyl), and the like.

Further in this regard, the synthesis of octahydro-BINAP is described in U.S. Pat. No. 5,206,399.

In addition, the phosphine compounds represented by the following general formula (IV) can similarly be used in the present invention:

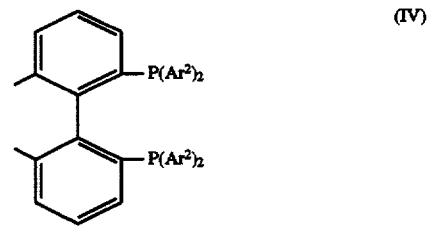
(IV)

wherein $Ar^2$ is a p-methoxyphenyl, phenyl, p-tolyl, m-tolyl, p-chlorophenyl or 3,5-xylyl group.

Specific examples of the phosphine compound represented by general formula (IV) include (4,4',6,6'-tetramethyl-5,5'-dimethoxybiphenyl-2,2'-diyl)-bis(diphenylphosphine) and (4,4',6,6'-tetramethyl-5,5'-dimethoxybiphenyl-2,2'-diyl)-bis(di-p-methoxyphenylphosphine), which compounds are described on page 1085 of *Chem. Pharm. Bull.*, vol. 39 (1991). Moreover, (4,4',6,6'-tetratrifluoromethyl-5,5'-dimethylbiphenyl-2,2'-diyl)-bis(diphenylphosphine) and (4,6,-ditrifluoromethyl-4,'6'dimethyl-5'-methoxybiphenyl-2,2'-diyl)-bis(diphenylphosphine) can also be used, which compounds are disclosed on page 827 of *Synlett* (1991). Furthermore, 2-dicyclohexyl-2'-diphenylphosphino-4,4',6,6'-tetramethyl-5,5'-dimethoxybiphenyl-2,2'-diyl)-bis(diphenylphosphine) can also be used, which compound is described on page 13 of *Tetrahedron: Asymmetry*, vol. 3 (1992).

Additional examples of other optically active tertiary phosphine compounds for use in the present invention are disclosed in Japanese Patent Publication No. 4-15796. These compounds include, for example, (6,6'-dimethyl-2,2'-biphenylene)-bis(diphenylphosphine), (4,4',6,6'-tetramethyl-2,2'-biphenylen)-bis(diphenylphosphine), (3,3',6,6'-tetramethyl-2,2'-biphenylen)-bis(diphenylphosphine), (4,4'-difluoro-6,6'-dimethyl-2,2'-biphenylene)-bis(diphenylphosphine), (4,4'-bis(dimethylamino)-6,6'-dimethyl-2,2'-biphenylene)-bis(diphenylphosphine), (6,6'-dimethyl-2,2'-biphenylene)-bis(di-p-tolylphosphine),(6,6'- dimethyl-2,2'-biphenylene)-bis(di-o-tolylphosphine),(6,6'-dimethyl-2,2'-biphenylene)-bis(di-m-fluorophenylphosphine), 1,11-bis(diphenylphosphine)-5,7-dihydrodibenzo[c,e]oxepine, and the like.

In addition, the phosphine compounds disclosed in Japanese Patent Laid-Open No. 3-5492 can be used. Examples thereof include (6,6'-dimethoxybiphenyl-2,2'-diyl)-bis(diphenylphosphine), (5,5',6,6'-tetramethoxybiphenyl-2,2'-diyl)-bis(diphenylphosphine),(6,6'-dimethoxybiphenyl-2,2'-diyl)-bis(di-p-tolylphosphine), (4,4',5,5',6,6'-hexamethoxybiphenyl-2,2'-diyl)-bis(diphenylphosphine), and the like.

Returning now to the iridium compounds which form a complex with the above described optically active phosphine compounds, useful examples thereof include di-μ-chlorobis(1,5-cyclooctadiene)diiridium as reported by J. L. Herde, J. C. Lambert and C. V. Senoff in *Inorg. Synth.*, 15 (1974), di-μ-chlorotetrakis(ethylene)diiridium described by A. L. Onderdelinden in *Inorg. Chim. Acta*, 6, 420 (1972) and by S. S. Bath and L. Vaska in *J. Chem. Soc.*, 85, 3500 (1963), and [Ir(COD)(CH$_3$CN)$_2$]Y, wherein COD represents 1,5-cyclooctadiene and Y represents BF$_4$, PF$_6$, ClO$_4$ or BPh$_4$, as disclosed in Japanese Patent Laid-Open No. 4-139192.

A complex obtained by reacting in situ the iridium compound with the above-described optically active phosphine compound may be used as the catalyst, or the complex may first be isolated prior to use.

Additional details with regard to preparation of the phosphine compound and complex with the iridium compound may be found by reference to M. Green et al., *J. Chem. Soc.*, (A) 2334 (1971), U.S. Pat. No. 5,159,093, M. A. Bennett and D. L. Milner, *J. Am. Chem. Soc.*, 91, 6983 (1969), U.S. Pat. No. 4,556,740 and U.S. Pat. No. 5,302,738.

Examples of the benzylamine derivative for use as an additive include p-methoxybenzylamine, 3,4-dimethoxybenzylamine, p-tolylbenzylamine, p-chlorobenzylamine, o-chlorobenzylamine and m-chlorobenzylamine.

The benzylamine derivative includes compounds represented by the following general formula (V):

(V)

where at least one of X, Y and Z is an aryl group (e.g., a C$_{6-12}$ aryl group) which may be substituted with a halogen atom (e.g., Cl, Br, I), a lower alkyl group (e.g., a C$_{1-4}$ alkyl group) or a lower alkoxy group (e.g., a C$_{1-4}$ alkoxy group) and the other of X, Y and Z are H.

The asymmetric hydrogenation is carried out as follows. The imine compound, which is the substrate for hydrogenation, is dissolved in an alcoholic solvent, such as methanol, ethanol and butanol, tetrahydrofuran, methylene chloride, benzene, or a mixture thereof. 1/100 to 1/1000 mole of the catalyst (i.e., the iridium-optically active phosphine complex) per 1 mole of the substrate is added to the solution, and 5 to 50 moles of benzylamine or a benzylamine derivative per 1 mole of the catalyst is further added thereto. Then, the mixture is subjected to hydrogenation in a hydrogen atmosphere at a pressure of from 10 to 100 kg/cm$^2$, preferably at a pressure of from 30 to 70 kg/cm$^2$, and at a temperature of from 5° to 100° C., preferably from 10° to 20° C., to provide an optically active amine compound.

EXAMPLES

The present invention is further described by reference to the following Examples and Comparative Examples.

However, the present invention should not be construed as being limited thereto.

Data for each compound was determined using the analytical instruments described below.

1H-NMR: AM-400 (400 MHz) (manufactured by Bruker Inc.) Optical purity: High Pressure Liquid Chromatography; LC-6A (manufactured by Shimadzu Corporation)

Chemical purity: GL Sciences Inc.; GC-9A (manufactured by Shimadzu Corporation)

Column: Silica capillary OV-101 25 m (manufactured by Gas Chromatography Kabushiki Kaisha)

Example 1

9.3 mg (0.0138 mmol) of [Ir(COD)Cl]$_2$, 19.9 mg (0.029 mmol) of (S)-2,2'-bis(di-p-tolylphosphino)-1,1'-binaphthyl, and 580 mg (2.76 mmol) of benzylimine prepared from acetophenone were poured into a 50 ml autoclave. After the atmosphere was replaced with argon, 2.2 ml of methanol was added thereto, followed by stirring. Then 15 μl (0.13 mmol) of benzylamine was added thereto and the mixture was stirred for 18 hours at 20° C. under a hydrogen atmosphere pressure of 60 kg/cm$^2$. The reaction solution was concentrated under reduced pressure and subjected to distillation in a claisen flask to provide 450 mg of a hydrogenated product. From the results of a 1H NMR spectrum, the product thus obtained was identified to be N-benzylphenethylamine.

The physical and chemical data of the product were determined as follows:

1H NMR(CDCl$_3$); 7.16–7.38 (m,10H), 3.76–3.04 (m,1H), 3.52–3.68 (m,2H), 1.56 (s,1H), 1.38 (d,3H).

The optical purity of the amine obtained from the above hydrogenation was 77% e.e. as determined by a Chiracel OD (manufactured by Daicel Chemical Industries, Ltd. 0.46 cm×25 cm) using hexane/ethyl acetate (98/2) as an eluent at a flow rate of 0.3 ml/min.

Comparative Example 1

An amine compound was prepared according to a process similar to that employed in Example 1, except that benzylamine was not used. This resulted in an optical purity of 23% e.e.

Example 2

9.3 mg (0.0138 mmol) of [Ir(COD)Cl]$_2$, 19.4 mg (0.0286 mmol) of (S)-2,2'-bis(di-p-tolylphosphino)-1,1'-binaphthyl, 2.2 ml of methanol, and 15 μl (0.137 mmol) of benzylamine were poured into a 50 ml autoclave, and then, 0.41 g (2.78 mmol) of 2-phenyl-3,4,5,6-tetrahydropyridine was added thereto. Hydrogenation was carried out for 20 hours at 20° C. under a hydrogen atmosphere pressure of 60 kg/cm$^2$. The reaction solution was concentrated under reduced pressure and subjected to distillation in a claisen flask to provide 0.344 g of a hydrogenated product. From the results of a 1H NMR spectrum, the product thus obtained was identified to be 2-phenylpiperidine.

The physical and chemical data of the product were determined as follows:

1H NMR(CDCl$_3$); 7.18–7.42 (m,10H), 3.52–3.64 (m,1H), 3.15–3.25 (m,1H), 2.72–2.88 (m,1H), 1.86–1.96 (m,1H), 1.72–1.86 (m,1H), 1.58–1.70 (m,2H), 1.42–1.58 (M,3H).

The optical purity of the amine obtained from the above hydrogenation was 91% e.e. as determined by a Chiracel OD (manufactured by Daicel Chemical Industries, Ltd.).

Comparative Example 2

An amine compound was hydrogenated according to a process similar to that employed in Example 2, except that benzylamine was not used. This resulted in an optical purity of 39% e.e.

Example 3

9.2 mg (0.0137 mmol) of [Ir(COD)Cl]$_2$, 19.9 mg (0.0293 mmol) of (S)-2,2'-bis(di-p-tolylphosphino)-1,1'-binaphthyl, 2.2 ml of methanol, and 15 μl (0.138 mmol) of benzylamine were poured into a 50 ml egg-plant shape flask with a three-way stop-cock, and then, 703 mg (2.71 mmol) of N{1-(2-naphthyl)ethylidene}benzylamine (the imine compound) was added thereto, followed by stirring for 1 hour. The resultant solution was poured into an autoclave. Hydrogenation was carried out for 18 hours at 20° C. under a hydrogen atmosphere pressure of 60 kg/cm$^2$. The reaction solution was concentrated under reduced pressure and subjected to silica gel chromatography to remove the catalyst, to thereby provide 680 mg of a hydrogenated product.

From the results of a 1H NMR spectrum, the product thus obtained was identified to be N-benzyl-1-(2-naphthyl)ethylamine.

The physical and chemical data of the product were determined as follows:

1H NMR(270 MHz,CD$_3$Cl); 7.72–7.88 (m,5H), 7.38–7.56 (m,3H), 7.15–7.35 (m,5H), 3.92–4.02 (q,1H), 3.59–3.73 (dd,2H), 1.62 (s,1H), 1.44 (d,3H).

The optical purity of the amine obtained from the above hydrogenation was 70% e.e. as determined by a Chiracel OD (manufactured by Daicel Chemical Industries, Ltd.).

Example 4

9.3 mg (0.0138 mmol) of [Ir(COD)Cl]$_2$, 19.8 mg (0.0292 mmol) of (S)-2,2'-bis(di-p-tolylphosphino)-1,1'-binaphthyl, 2.2 ml of methanol, and 15 μl (0.138 mmol) of benzylamine were poured into a 50 ml egg-plant shape flask with a three-way stop-cock, and then, 590 μl (2.76 mmol) of N-(1-cyclohexylethylidene)benzylamine (the imine compound) was added thereto, followed by stirring for 1 hour. The resultant solution was poured into an autoclave. Hydrogenation was carried out for 18 hours at 20° C. under a hydrogen atmosphere pressure of 60 kg/cm$^2$. The reaction solution was concentrated under reduced pressure and subjected to Kugel distillation to remove the catalyst, to thereby provide 463 mg of a hydrogenated product.

From the result of a 1H NMR spectrum, the product thus obtained was identified to be N-benzyl-1-cyclohexylethylamine.

The physical and chemical data of the product were determined as follows:

1H NMR(270 MHz,CD$_3$Cl); 7.18–7.38 (m,5H), 3.65–3.90 (dd,2H), 2.44–2.56 (m,1H), 1.60–1.82 (m,5H), 0.93–1.43 (m,10H)

The optical purity of the amine obtained from the above hydrogenation was 73% e.e. as determined by a Chiracel OD (manufactured by Daicel Chemical Industries, Ltd.).

While the invention has been described in detail and with reference to specific embodiments thereof, it will be apparent to one skilled in the art that various changes and modifications can be made therein without departing from the spirit and scope thereof.

What is claimed is:

1. A process for preparing an optically active amine compound which comprises asymmetrically hydrogenating an imine compound having the following general formula (I)

wherein $R^1$, $R^2$ and $R^3$ each represents an aromatic hydrocarbon group, an aliphatic hydrocarbon group or an alicyclic hydrocarbon group, and two of $R^1$, $R^2$ and $R^3$ may bond together to form a 5- or 6-membered ring in the presence of a catalytic amount of an iridium-optically active phosphine complex and benzylamine or a benzylamine derivative.

2. A process for preparing an optically active amine compound as set forth in claim 1, wherein the optically active phosphine of said iridium-optically active phosphine complex is represented by the following general formula (II):

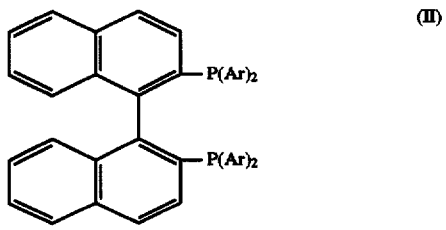

wherein Ar is a phenyl group which may be para- and/or meta-substituted with one or more lower alkyl groups.

3. A process for preparing an optically active amine compound as set forth in claim 1, wherein the optically active phosphine of said iridium-optically active phosphine complex is represented by the following general formula (III):

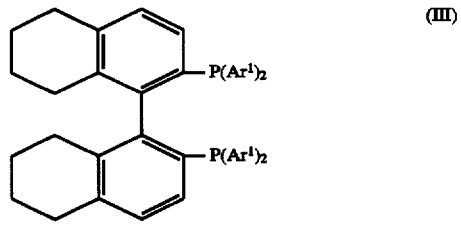

wherein $Ar^1$ is a p-methoxyphenyl, phenyl, p-tolyl, m-tolyl, p-chlorophenyl or 3,5-xylyl group.

4. A process for preparing an optically active amine compound as set forth in claim 1, wherein the optically active phosphine of said iridium-optically active phosphine complex is represented by the following general formula (IV):

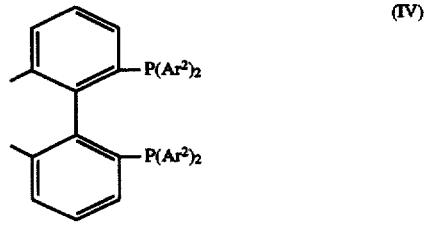

wherein $Ar^2$ is a p-methoxyphenyl, phenyl, p-tolyl, m-tolyl, p-chlorophenyl or 3,5-xylyl group.

5. A process for preparing an optically active amine compound as set forth in claim 1, wherein the aromatic hydrocarbon group represented by $R^1$, $R^2$ and $R^3$ is unsubstituted.

6. A process for preparing an optically active amine compound as set forth in claim 1, wherein the aliphatic hydrocarbon group represented by $R^1$, $R^2$ and $R^3$ is unsubstituted.

7. A process for preparing an optically active amine compound as set forth in claim 1, wherein the alicyclic hydrocarbon group represented by $R^1$, $R^2$ and $R^3$ is unsubstituted.

8. A process for preparing an optically active amine compound as set forth in claim 1, wherein the aromatic hydrocarbon group represented by $R^1$, $R^2$ and $R^3$ is substituted with a halogen atom, a lower alkyl group or a lower alkoxy group.

9. A process for preparing an optically active amine compound as set forth in claim 1, wherein the aliphatic hydrocarbon group represented by $R^1$, $R^2$ and $R^3$ is substituted with a halogen atom, a lower alkyl group, a lower alkoxy group or said aromatic hydrocarbon group represented by $R^1$, $R^2$ and $R^3$.

10. A process for preparing an optically active amine compound as set forth in claim 1, wherein the alicyclic hydrocarbon group represented by $R^1$, $R^2$ and $R^3$ is substituted with a halogen atom, a lower alkyl group, a lower alkoxy group or said aromatic hydrocarbon group represented by $R^1$, $R^2$ and $R^3$.

11. A process for preparing an optically active amine compound as set forth in claim 1, wherein the imine compound represented by formula (I) is the condensation product of benzylamine and a ketone.

12. A process for preparing an optically active amine compound as set forth in claim 1, wherein the imine compound represented by formula (I) is a cyclic imine compound.

13. A process for preparing an optically active amine compound as set forth in claim 12, wherein the imine compound represented by formula (I) is selected from the group consisting of 3,4-dihydro-5-methyl-2H-pyrrole, 5-n-butyl-3,4-dihydro-2H-pyrrole, 3,4-dihydro-5-ethyl-2H-pyrrole, 3,4-dihydro-5-phenyl-2H-pyrrole, 2-methyl-3,4,5,6-tetrahydropyridine and 2-phenyl-3,4,5,6-tetrahydropyridine.

14. A process for preparing an optically active amine compound as set forth in claim 1, wherein the benzylamine derivative is selected from the group consisting of p-methoxybenzylamine, 3,4-dimethoxybenzylamine, p-tolylbenzylamine, p-chlorobenzylamine, o-chlorobenzylamine and m-chlorobenzylamine.

15. A process for preparing an optically active amine compound as set forth in claim 1, comprising asymmetrically hydrogenating an imine compound represented by formula (I) in the presence of 1/100 to 1/1000 mole of the iridium-optically active phosphine complex per mole of the imine compound and 5 to 50 moles of benzylamine or a benzylamine derivative per mole of the iridium-optically active phosphine complex.

16. A process for preparing an optically active amine compound as set forth in claim 1, comprising asymmetrically hydrogenating an imine compound represented by formula (I) in the presence of the iridium-optically active phosphine complex and benzylamine or a benzylamine derivative in a hydrogen atmosphere at a pressure of from 10 to 100 kg/cm² and at a temperature of from 5° to 100° C.

17. A process for preparing an optically active amine compound which comprises asymmetrically hydrogenating an imine compound having the following general formula (I)

wherein $R^1$, $R^2$ and $R^3$ each represents (i) an aromatic hydrocarbon group which may be substituted with a halogen atom, a lower alkyl group or a lower alkoxy group, (ii) an aliphatic hydrocarbon group which may be substituted with a halogen atom, a lower alkyl group, a lower alkoxy group or said aromatic hydrocarbon group, or (iii) an alicyclic hydrocarbon group which may be substituted with a halogen atom, a lower alkyl group, a lower alkoxy group or said aromatic hydrocarbon group, and two of $R^1$, $R^2$ and $R^3$ may bond together to form a 5- or 6-membered ring in the presence of a catalytic amount of an iridium-optically active phosphine complex and benzylamine or a benzylamine derivative.

* * * * *